United States Patent [19]

Hill

[11] Patent Number: 5,705,562
[45] Date of Patent: Jan. 6, 1998

[54] SPONTANEOUSLY FORMED CLEAR SILICONE MICROEMULSIONS

[75] Inventor: Randal Myron Hill, Midland, Mich.

[73] Assignee: Dow Corning Corporation, Midland, Mich.

[21] Appl. No.: 560,561

[22] Filed: Nov. 20, 1995

[51] Int. Cl.⁶ .................................................. C08K 5/24
[52] U.S. Cl. .......................... 524/731; 524/837; 524/268; 524/457
[58] Field of Search ................................. 524/837, 731, 524/268, 457

[56] References Cited

U.S. PATENT DOCUMENTS 3,299,112  1/1967  Bailey ........................... 260/448.2
4,999,398  3/1991  Graiver et al. ...................... 524/837

OTHER PUBLICATIONS

"Microemulsions Theory & Practice", Leon M. Prince, Academic Press, pp. 7-10, (1977).

Primary Examiner—Karen A. Dean
Attorney, Agent, or Firm—James L. DeCesare

[57] ABSTRACT

A method of spontaneously forming a highly stable clear microemulsion by combining (i) water; (ii) a volatile cyclic methyl siloxane or volatile linear methyl siloxane; and (iii) a silicone polyether surfactant. The amounts of each component are such that the composition is in the form of a microemulsion. The volatile methyl siloxane is present in the microemulsion in the form of particles having an average diameter of less than about 100 nanometers. The microemulsion is useful in personal care products.

6 Claims, 1 Drawing Sheet

SPONTANEOUSLY FORMED CLEAR SILICONE MICROEMULSIONS

BACKGROUND OF THE INVENTION

This invention is directed to an optically clear silicone microemulsion formed with very little input of mechanical energy for mixing the components. More particularly, a ternary composition of water, a volatile cyclic or linear methyl siloxane (VMS), and a short-chain or low molecular weight silicone polyether, spontaneously provides optically clear microemulsions when combined with only hand agitation.

It is well documented (U.S. Pat. No. 4,999,398) that emulsions, especially silicone emulsions, are opaque, cloudy, and tend to separate on standing. Thus, the desirability of microemulsions, which contain micro-particles in the droplet phase, providing a measure of clarity.

As used herein, the term emulsion or macroemulsion means a dispersion of one immiscible liquid in another, in the form of droplets, with diameters approximately in the range of 100–1,000 nanometers (0.1–1.0 microns/1,000–10,000 angstroms Å). In contrast, a microemulsion means a transparent, thermodynamically stable, dispersion of two or more immiscible liquids and a surfactant.

Microemulsions are clear or transparent because they contain particles smaller than the wavelength of visible light, which is typically on order of about 10–100 nanometers. Microemulsions may contain oil droplets dispersed in water (O/W), water droplets dispersed in oil (W/O), or they may be in the form of a bicontinuous structure. They are characterized by an ultra-low interfacial tension between the oil and water phases.

A microemulsion can be recognized by several of its inherent characteristics which are that (i) it contains oil, water, and a surfactant; (ii) there is a high concentration of surfactant relative to oil; (iii) the system is optically clear; (iv) the phases do not separate by centrifugation; and (v) the system forms spontaneously.

Thus, for purposes of my invention, an emulsion is considered as containing particles having an average diameter of more than 100 nanometers (0.1 microns/1,000 angstroms Å), whereas a microemulsion contains particles having an average diameter of less than 100 nanometers (0.1 microns/1,000 angstroms Å). Clarity or transparency is controlled to a great extent by the particle size of the dispersed phase. The scattering of light is dependent on the particle size. Therefore, clear or transparent compositions appear to be a single phase without droplets or particles when viewed with the naked eye, as defined hereafter.

While Bailey in U.S. Pat. No. 3,299,112 describes emulsions formed from water, a silicone oil, and a silicone polyether, Bailey's emulsions are not clear; and require input of substantial mechanical energy to prepare. Furthermore, in contrast to my invention, the ternary system in the '112 patent is not a microemulsion; the silicone oil is not a volatile cyclic VMS; and where Bailey does describe a linear silicone oil, it is not a volatile linear silicone. Thus, the silicone oil in Bailey corresponds to $R''_3SiO(R''_2SiO)_xSiR''_3$ where x is 10–1,000. My corresponding volatile linear VMS have an "x" of 0–5, well below the range in Bailey. In fact, I discovered that where "x" exceeds 5, the emulsions tend not to be clear.

In addition, emulsions are recognized as inherently unstable systems separating with time. In contrast, my microemulsions form spontaneously and are stable indefinitely. The order of addition of the components does not influence their formation, and simple hand shaking in the temperature range of their stability is sufficient to cause the microemulsions to form.

My spontaneously formed clear microemulsions have particular value in the personal care arena. Because of the unique volatility characteristics of the VMS component of my ternary system, it can be used alone, or blended with other cosmetic fluids, to form a variety of over-the-counter personal care products.

Thus, it is useful as a carrier in antiperspirants and deodorants, since it leaves a dry feel, and does not cool the skin upon evaporation. It is lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats, to enhance gloss and drying time, and provide conditioning benefits. In cosmetics, it will function as a leveling and spreading agent for pigments in make-ups, color cosmetics, foundations, blushes, lipsticks, eyeliners, mascaras, oil removers, color cosmetic removers, and powders. It is useful as a delivery system for oil and water soluble substances such as vitamins. When incorporated into sticks, gels, lotions, aerosols, and roll-ons, my ternary composition imparts a dry, silky-smooth, payout.

In addition, because my spontaneously formed clear microemulsions exhibit a variety of advantageous and beneficial properties such as (i) clarity, (ii) very small particle size, (iii) ultra-low interfacial tensions, (iv) the ability to combine properties of water and oil in a single homogeneous fluid, (v) shelf stability, and (vi) ease of preparation; they have wide application, but especially in antiperspirants, deodorants, in perfumes as a carrier, and hair conditioning.

BRIEF SUMMARY OF THE INVENTION

It is an object of my invention to form a clear microemulsion by simply combining (i) water; (ii) a volatile cyclic methyl siloxane or volatile linear methyl siloxane; and (iii) a silicone polyether.

What I have accomplished is significant, because I discovered how to make clear products without involving the use of high shear, heretofore required to obtain the small particle size necessary to achieve clarity.

These clear microemulsions form spontaneously in the sense that they do not require energy input by means of mixing and shear devices. Thus, turbines, impellers, colloid mills, homogenizers, or sonolators, are not required to form these systems. It is only necessary that the appropriate amounts of the three components be added to a suitable container, and the container hand shaken. Of course, the components can be mixed or sheared with more energy input, and the microemulsions will still be obtained, but no advantage results from such additional energy usage.

These and other objects of my invention will become apparent from a consideration of the detailed description.

BRIEF DESCRIPTION OF THE DRAWINGS

In FIGURE 1, each of the corners represents 100 percent of the component labelled there. The side of the triangle directly opposite each corner represents zero percent of that component. Lines parallel to the opposite side represent increasing amounts of that component as they become closer to the corner. Any line drawn from the corner of Component A to the opposite side represents varying the amount of Component A at a constant ratio of the other two components.

Figure 1:
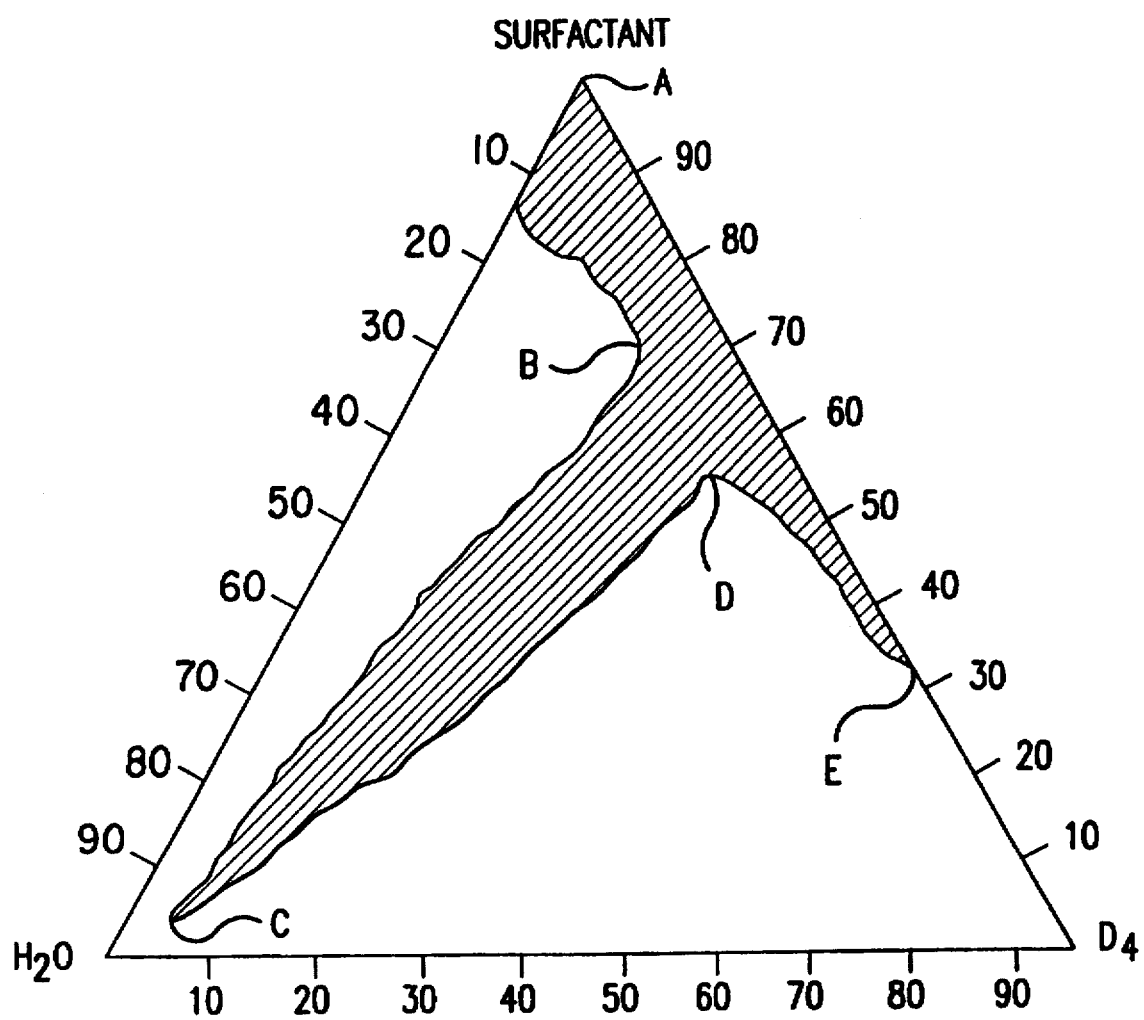
FIGURE 1 is a ternary phase diagram of the system comprising water, octamethylcyclotetrasiloxane ($D_4$), and the silicone surfactant, for determining composition ranges of microemulsions prepared according to Example XIII of my invention. The compositions are defined by the shaded area depicted in FIGURE 1.

The composition of any point within the shaded area is determined by drawing lines parallel to each of the three sides through the point. The amount of each component is then read from the intersection of each line with the side of the triangle which corresponds to that component, i.e. the side beginning at 100 at each component's corner.

DETAILED DESCRIPTION

My ternary composition contains water, a volatile cyclic or linear methyl siloxane (VMS), and a short-chain or low molecular weight silicone polyether. Those three components can be combined to form clear compositions without the addition of other materials.

Thus, the composition should be free of non-essential ingredients such as salts; co-surfactants; monohydroxy alcohols; and diols and triols such as ethylene glycol and glycerol. The elimination of such non-essential ingredients is especially beneficial and advantageous, as it obviates the need for refractive index matching, often resorted to in the past to achieve clear or transparent products.

The three components can be combined in any given order of addition. While heat enhances solubility, lowers surface tension, and reduces viscosity, its application is not required. Room temperature (20°–25° C./68°–77° F.) is sufficient in most cases.

The oil component of my ternary composition is a volatile methyl siloxane (VMS), which is a low viscosity silicone fluid corresponding to the average unit formula $(CH_3)_a SiO_{(4-a)/2}$ in which a has an average value of two or three. The fluid contains siloxane units joined by $\equiv Si-O-Si\equiv$ bonds. Representative units are monofunctional "M" units $(CH_3)_3 SiO_{1/2}$ and difunctional "D" units $(CH_3)_2 SiO_{2/2}$. The presence of trifunctional "T" units $CH_3 SiO_{3/2}$ results in the formation of branched cyclic volatile methyl siloxanes. The presence of tetrafunctional "Q" units $SiO_{4/2}$ results in the formation of branched linear volatile methyl siloxanes.

Linear VMS have the formula $(CH_3)_3SiO\{(CH_3)_2SiO\}_xSi(CH_3)_3$, and cyclic VMS have the formula $\{(CH_3)_2SiO\}_y$, in which x is 0–5, and y is 3–6. Preferably, the volatile methyl siloxane has a boiling point less than 250° C. and a viscosity of 0.65–5.0 centistokes (mm²/s).

Some representative volatile methyl siloxanes are:

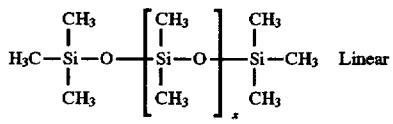

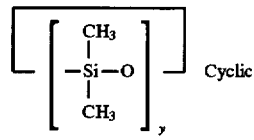

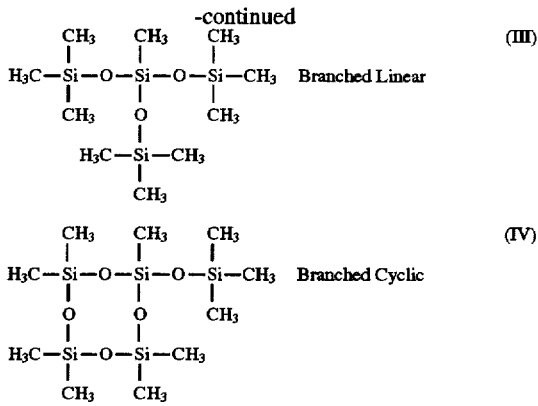

The cyclic volatile methyl siloxanes (II) have been assigned the International Nomenclature Cosmetic Ingredient (INCI) name "CYCLOMETHICONE" by The Cosmetics, Toiletries and Fragrance Association, Inc., (CTFA) Washington, D.C. Cyclic and linear methyl siloxanes are clear fluids, essentially odorless, non-toxic, non-greasy, non-stinging, and non-irritating to skin. VMS leave substantially no residue after thirty minutes at room temperature (20°–25° C./68°–77° F.) when one gram is placed at the center of No. 1 circular filter paper of 185 millimeters diameter, supported at its perimeter in open room atmosphere. Volatile methyl siloxanes may be used alone or mixed together. Mixtures result in solutions having evaporating behaviors different from individual fluids.

Representative linear volatile methyl siloxanes (I) are hexamethyldisiloxane (MM) with a boiling point of 100° C., viscosity of 0.65 mm²/s, and formula $Me_3SiOSiMe_3$; octamethyltrisiloxane (MDM) with a boiling point of 152° C., viscosity of 1.04 mm²/s, and formula $Me_3SiOMe_2SiOSiMe_3$; decamethyltetrasiloxane (MD₂M) with a boiling point of 194° C., viscosity of 1.53 mm²/s, and formula $Me_3SiO(Me_2SiO)_2SiMe_3$; dodecamethylpentasiloxane (MD₃M) with a boiling point of 229° C., viscosity of 2.06 mm²/s, and formula $Me_3SiO(Me_2SiO)_3SiMe_3$; tetradecamethylhexasiloxane (MD₄M) with a boiling point of 245° C., viscosity of 2.63 mm²/s, and formula $Me_3SiO(Me_2SiO)_4SiMe_3$; and hexadecamethylheptasiloxane (MD₅M) with a boiling point of 270° C., viscosity of 3.24 mm²/s, and formula $Me_3SiO(Me_2SiO)_5SiMe_3$.

Representative cyclic volatile methyl siloxanes (II) are hexamethylcyclotrisiloxane (D₃) a solid with a boiling point of 134° C. and formula $\{(Me_2)SiO\}_3$; octamethylcyclotetrasiloxane (D₄) with a boiling point of 176° C., viscosity of 2.3 mm²/s, and formula $\{(Me_2)SiO\}_4$; decamethylcyclopentasiloxane (D₅) with a boiling point of 210° C., viscosity of 3.87 mm²/s, and formula $\{(Me_2)SiO\}_5$; and dodecamethylcyclohexasiloxane (D₆) with a boiling point of 245° C., viscosity of 6.62 mm²/s, and formula $\{(Me_2)SiO\}_6$.

Representative branched volatile methyl siloxanes (III) and (IV) are heptamethyl-3-{(trimethylsilyl)oxy}trisiloxane (M₃T) with a boiling point of 192° C., viscosity of 1.57 mm²/s, and formula $C_{10}H_{30}O_3Si_4$; hexamethyl-3,3,bis{(trimethylsilyl)oxy} trisiloxane (M₄Q) with a boiling point of 222° C., viscosity of 2.86 mm²/s, and formula $C_{12}H_{36}O_4Si_5$; and pentamethyl {(trimethylsilyl)oxy} cyclotrisiloxane (MD₃) with the formula $C_8H_{24}O_4Si_4$.

One preferred VMS component of my ternary system is octamethylcyclotetrasiloxane $[(CH_3)_2SiO]_4$. It has a viscosity of 2.3 centistokes (mm²/s) at 25° C., and is referred to as "D₄" since it contains four difunctional "D" units $(CH_3)_2SiO_{2/2}$ shown as:

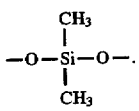

Four "D" units combine to form octamethylcyclotetrasiloxane shown in either formula below:

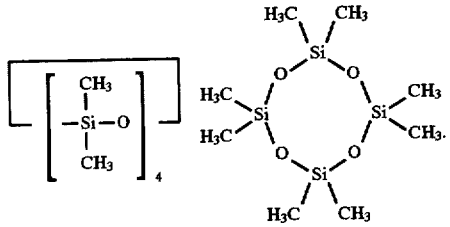

In the literature, $D_4$ is often called CYCLOMETHICONE or TETRAMER. It has a higher viscosity (2.3 cs) and is thicker than water (1.0 cs), yet octamethylcyclotetrasiloxane needs 94% less heat to evaporate than water.

Another preferred VMS component of my ternary system is decamethylcyclopentasiloxane (D5) often referred to as PENTAMER. It is shown structurally below:

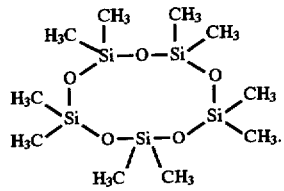

A benefit offered by using VMS compounds is that many local, state, federal, and international regulations, have restricted the use of certain chemicals, but VMS is a suitable replacement. Thus, the Environmental Protection Agency (EPA) determined that volatile methyl siloxanes such as octamethylcyclotetrasiloxane, decamethylcyclopentasiloxane, dodecamethylcyclohexasiloxane, hexamethyldisiloxane, octamethyltrisiloxane, and decamethyltetrasiloxane, were acceptable substitutes for the CFC-113 chlorofluorocarbon ($C_2Cl_3F_3$) and methylchloroform (MCF). This determination is limited to cleaning in closed systems, for metal cleaning, electronic cleaning, and precision cleaning applications, under the EPA's Significant New Alternatives Policy (SNAP).

In addition, the EPA excluded VMS as a volatile organic compound (VOC). Thus, they added VMS to a list of compounds in 40 CFR 51,100(s) excluded from the definition of VOC, on the basis that VMS compounds have negligible contribution to tropospheric ozone formation. They pointed out that exempting VMS from regulation as an ozone precursor contributes to achievement of several important environmental goals, in that VMS might be used as a substitute for compounds listed as hazardous air pollutants (HAP). As they explained, that met the need to develop substitutes for ozone depleting substances (ODS), and attained National Ambient Air Quality Standards for ozone under Title I of the Clean Air Act.

The other component of my ternary system, in addition to water and VMS, is a short-chain or low molecular weight silicone polyether. Representative polyether structures are:

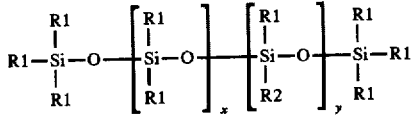

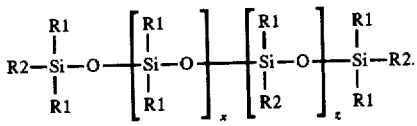

A cyclic polyether of the type shown below can also be used.

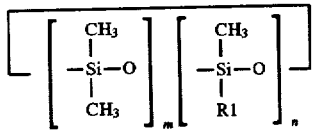

In these structures, R1 represents an alkyl group containing 1–6 carbon atoms such as methyl, ethyl, propyl, butyl, pentyl, and hexyl; R2 represents the radical —$(CH_2)_aO(C_2H_4O)_b(C_3H_6O)_cR3$; x has a value of 0–3; y has a value of 1–3; z has a value of 0–2; m has a value of 3–5; n is one; a has a value of 3–6; b has a value of 4–20; c has a value of 0–5; and R3 is hydrogen, a methyl radical, or an acyl radical such as acetyl. Preferably, R1 is methyl; b is 6–12; c is zero; and R3 is hydrogen.

Compositions according to my invention may contain 5–70% by weight of surfactant, but most preferably, they contain about 15–30% by weight of the surfactant. The balance of the composition is oil and water, with the proportions of oil and water generally falling between 40:60 to 80:20, or 0.4 to 0.8 as defined below for Ratio 1.

For purposes of my invention, the criteria used to determine optical clarity is whether text can be read with the naked eye through a two centimeter diameter bottle filled with the microemulsion.

As noted in the textbook *Microemulsions Theory and Practice*, Edited by Leon M. Prince, Academic Press, Inc., Pages 7–10, New York (1977), the "Visual recognition of microemulsions should not be taken lightly. In fact, the microemulsion chemist should train himself carefully in this art. Use of sunlight rather than an artificial source of light is recommended. The eye is better than a microscope because the limit of resolution of a light microscope in blue light is only about 0.1 µm so that droplets smaller than 0.14 µm cannot be seen".

The following examples show my invention in more detail.

EXAMPLE I

I formed optically clear microemulsions spontaneously at temperatures ranging between 47°–62° C. by merely adding to a container, 50 parts of de-ionized water, 50 parts of octamethylcyclotetrasiloxane (D4), and 25 parts of silicone polyether. No mixing, stirring, shearing, or input of mechanical energy for agitating the three ingredients was required. The polyether corresponded to the compound:

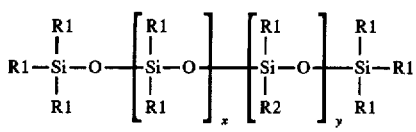

where R1 was methyl, x was zero, y was one, and R2 was —$(CH_2)_3(OC_2H_4)_8OH$. I was able to read text through a two centimeter diameter bottle filled with the microemulsions. I determined that the microemulsions contained particles having an average diameter of less than 100 nanometers (0.1 microns).

EXAMPLE II

I repeated Example I and formed clear microemulsions spontaneously at temperatures ranging between 60°–68° C. by merely combining in a container, 50 parts of de-ionized water, 50 parts of decamethylcyclopentasiloxane (D5), and 25 parts of silicone polyether. The optical clarity was the same as obtained in Example I.

EXAMPLE III

I repeated Example I and formed clear microemulsions spontaneously at temperatures ranging between 44°–60° C. by merely combining in a container, 60 parts of de-ionized water, 40 parts of octamethylcyclotetrasiloxane (D4), and 17.65 parts of silicone polyether. The optical clarity was the same as obtained in Example I.

EXAMPLE IV

I repeated Example III including the use of salt which is a non-essential ingredient. I formed clear microemulsions spontaneously at temperatures ranging between 20°–30° C. by merely combining in a container, 50 parts of an aqueous solution containing 15% sodium chloride, 50 parts of octamethylcyclotetrasiloxane (D4), and 17.65 parts of silicone polyether. The optical clarity was the same as obtained in Example III.

EXAMPLE V

I repeated Example IV and formed clear microemulsions spontaneously at temperatures ranging between 22°–41° C. by merely combining in a container, 30 parts of an aqueous solution containing 15% sodium chloride, 70 parts of octamethylcyclotetrasiloxane (D4), and 25 parts of silicone polyether. The optical clarity was the same as obtained in Example IV.

EXAMPLE VI

I repeated Example II and formed clear microemulsions spontaneously at temperatures ranging between 30°–85° C. by merely combining in a container, 50 parts of de-ionized water, 50 parts of decamethylcyclopentasiloxane (D5), and 66.67 parts of silicone polyether. The optical clarity was the same as obtained in Example II.

The following four examples illustrate preparation of clear antiperspirants. In Examples VII–X, an antiperspirant active was incorporated into my clear silicone microemulsion without input of mechanical energy for mixing the components.

EXAMPLE VII

I repeated Example I and formed clear microemulsions spontaneously at temperatures ranging between 42°–58° C. by merely combining in a container, 50 parts of an aqueous solution containing 25% of the antiperspirant active Aluminum Chlorohydrate (ACH-303), 50 parts of octamethylcyclotetrasiloxane (D4), and 25 parts of silicone polyether. The optical clarity was the same as obtained in Example I.

EXAMPLE VIII

I repeated Example VII and formed clear microemulsions spontaneously at temperatures ranging between 36°–69.6° C. by merely combining in a container, 50 parts of an aqueous solution containing 25% of the antiperspirant active Aluminum-Zirconium Tetrachlorohydrex-Gly (ACH-370), 50 parts of octamethylcyclotetrasiloxane (D4), and 28.2 parts of silicone polyether. The optical clarity was the same as obtained in Example VII.

EXAMPLE IX

I repeated Example VII and formed clear microemulsions spontaneously at temperatures ranging between 30°–46° C. by merely combining in a container, 50 parts of an aqueous solution containing 50% of the antiperspirant active Aluminum Chlorohydrate (ACH-303), 50 parts of octamethylcyclotetrasiloxane (D4), and 21.95 parts of silicone polyether. The optical clarity was the same as obtained in Example VII.

EXAMPLE X

I repeated Example VII and formed clear microemulsions spontaneously at room temperature by merely combining in a container, 63 parts of an aqueous solution containing 25% of the antiperspirant active Aluminum Chlorohydrate (ACH-303) and 15% of sodium chloride, 37 parts of octamethylcyclotetrasiloxane (D4), and 20.5 parts of silicone polyether. The optical clarity was the same as obtained in Example VII.

Other antiperspirant actives such as Aluminum Sesquichlorohydrate salts can be used in Examples VII–X. Suitable antiperspirants products can be formulated containing a maximum use level of antiperspirant active of 20% by weight AZG and 25% by weight ACH, on an anhydrous basis.

The following examples illustrate preparation of compositions according to my invention using a linear volatile methyl siloxane instead of a cyclic volatile methyl siloxane.

EXAMPLE XI

I repeated Example I and formed clear microemulsions spontaneously at temperatures ranging between 30°–70° C. by merely combining in a container, 50 parts of de-ionized water, 50 parts of hexamethyldisiloxane (MM), and 42.9 parts of silicone polyether. The optical clarity was the same as obtained in Example I.

EXAMPLE XII

I repeated Example XI and formed clear microemulsions spontaneously at temperatures ranging between 43°–56° C. by merely combining in a container, 50 parts of de-ionized water, 50 parts of hexamethyldisiloxane (MM), and 17.7 parts of silicone polyether. The optical clarity was the same as obtained in Example I.

Table I provides a summary of Examples I–XII. In Table I, Ratio 1 is the amount of oil divided by the amounts of oil and water. Ratio 2 is the amount of surfactant divided by the amounts of oil, water, and surfactant. Percent Surfactant is obtained from the relationship (Ratio 2) divided by (1–Ratio 2)×100.

TABLE I

| Example | Temperature (°C.) | Ratio 1 | Ratio 2 | % Surfactant |
|---|---|---|---|---|
| I | 47–62 | 0.5 | 0.2 | 25.0 |
| II | 60–68 | 0.5 | 0.2 | 25.0 |
| III | 44–60 | 0.4 | 0.15 | 17.6 |
| IV | 20–30 | 0.5 | 0.15 | 17.6 |
| V | 22–41 | 0.7 | 0.2 | 25.0 |
| VI | 30–85 | 0.5 | 0.4 | 66.7 |
| VII | 42–58 | 0.5 | 0.2 | 25.0 |
| VIII | 36–69.6 | 0.5 | 0.22 | 28.2 |
| IX | 30–46 | 0.5 | 0.18 | 22.0 |
| X | 20–25 | 0.5 | 0.22 | 28.2 |
| XI | 30–70 | 0.5 | 0.3 | 42.9 |
| XII | 43–56 | 0.5 | 0.15 | 17.6 |

As can be seen in Table I, compositions according to my invention can be prepared at temperatures generally in the range of 20°–85° C. They contain 5–70% by weight of surfactant, most preferably, about 15–30% by weight of the surfactant; with the balance being oil and water. The proportions of oil and water generally fall between 40:60 to 80:20, or 0.4 to 0.8 as defined above for Ratio 1.

EXAMPLE XIII

I formed a number of optically clear microemulsions spontaneously at room temperature (22° C.). In this example, compositions representative of my invention were prepared, wherein the mixing ratio of the three components comprising water, oil, and surfactant, was within the shaded area in FIGURE 1 of the drawing, i.e. the area surrounded by the lines connecting points A, B, C, D, and E. I formed these microemulsions in the same manner as in Example I. Thus, I merely added the three ingredients to a container. No mixing, stirring, shearing, or input of mechanical energy for agitating the three ingredients was required. The polyether corresponded to the same compound used in Example I. I was again able to read text through a two centimeter diameter bottle filled with these microemulsions. They contained particles having an average diameter of less than 100 nanometers (0.1 microns).

EXAMPLE XIV—COMPARISON

I repeated Example I and formed a number of emulsions at room temperature. However, in this COMPARISON EXAMPLE, I used a silicone oil equivalent to the silicone oils described in Bailey's U.S. Pat. No. 3,299,112. Thus, Bailey's silicone oil is said to correspond to $R''_3SiO(R''_2SiO)_xSiR''_3$ with x being 10–1,000. I followed the teaching in Bailey, but was not able to read text through a two centimeter diameter bottle filled with these Bailey emulsions. As noted in the BACKGROUND OF THE INVENTION, my invention in one embodiment involves using a volatile linear VMS having an "x" of 0–5, well below the range in Bailey. In this COMPARISON EXAMPLE, I verified that where "x" exceeds 5, the compositions are not clear.

Other variations may be made in the compounds, compositions, or methods described, without departing from the essentials of my invention, the forms of which are exemplary, and not limitations on its scope as defined in the claims.

I claim:

1. A method comprising spontaneously forming a microemulsion without mixing, stirring, shearing, or input of mechanical energy for agitating ingredients used to make a microemulsion, by simply combining (i) water; (ii) a cyclic methyl siloxane having the formula $\{(CH_3)_2SiO\}_p$ or a linear methyl siloxane having the formula $(CH_3)_3SiO\{(CH_3)_2SiO\}_qSi(CH_3)_3$ in which p is 3–6 and q is 0–5; and (iii) a silicone polyether having a formula selected from the group consisting of

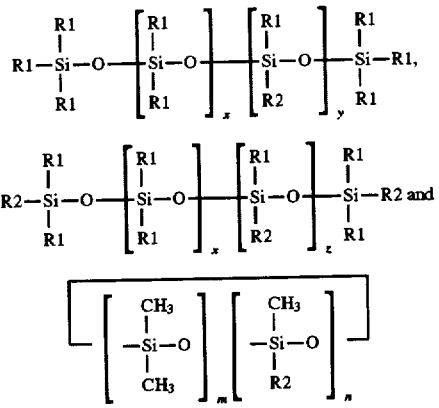

where R1 represents an alkyl group containing 1–6 carbon atoms; R2 represents the radical $-(CH_2)_aO(C_2H_4O)_b(C_3H_6O)_cR3$; x has a value of 0–3; y has a value of 1–3; z has a value of 0–2; m has a value of 3–5; n is one; a has a value of 3–6; b has a value of 4–20; c has a value of 0–5; and R3 is hydrogen, a methyl radical, or an acyl radical.

2. A method according to claim 1 in which the methyl siloxane is present in the microemulsion in the form of droplets having an average diameter of less than 100 nanometers.

3. A method according to claim 1 in which the methyl siloxane is octamethylcyclotetrasiloxane.

4. A method according to claim 1 in which the methyl siloxane is decamethylcyclopentasiloxane.

5. A microemulsion prepared according to the method defined in claim 1.

6. A microemulsion prepared according to the method defined in claim 3, the microemulsion having a composition defined by and within the shaded area depicted in the annexed sole FIGURE 1.

* * * * *